United States Patent [19]  [11]  4,258,055
Lietti et al.  [45]  Mar. 24, 1981

[54] PHARMACEUTICAL COMPOSITIONS

[75] Inventors: Andrea Lietti; Attilio Bonati, both of Milan, Italy

[73] Assignee: Inverni Della Beffa S.p.A., Milan, Italy

[21] Appl. No.: 59,183

[22] Filed: Jul. 20, 1979

Related U.S. Application Data

[60] Division of Ser. No. 881,892, Feb. 27, 1978, which is a continuation-in-part of Ser. No. 829,912, Sep. 1, 1977, abandoned.

[30] Foreign Application Priority Data

Sep. 8, 1976 [GB] United Kingdom .............. 37252/76

[51] Int. Cl.³ .............................................. A61K 31/35
[52] U.S. Cl. .................................................... 424/283
[58] Field of Search ......................................... 424/283

[56] References Cited

PUBLICATIONS

Chem. Abst., 9th Coll. Subj. Index–Chem. Substances, pp. 7002CS & 6995CS.

*Primary Examiner*—Stanley J. Friedman
*Attorney, Agent, or Firm*—Browdy and Neimark

[57] ABSTRACT

Valuable pharmaceutical properties of flavylium salts are described, including anti-inflammatory, vaso-protective, hypolipaemic, hypocholesterolaemic and hypoglycaemic activity. The use of flavylium salts as drugs and the production of pharmaceutical compositions containing them is particularly referred to.

5 Claims, No Drawings

PHARMACEUTICAL COMPOSITIONS

This is a division of application Ser. No. 881,892 filed Feb. 27, 1978, which in turn is a continuation-in-part application of Ser. No. 829,912 filed Sept. 1, 1977, now abandoned.

This invention relates to pharmaceutical compositions and processes for their preparation.

Anthocyanidines are a group of known polyphenolic substances. These products, which more precisely are flavylium salts, as well as being preparable by total chemical synthesis, may be obtained by hydrolysis of their glycosides which are widely distributed in nature. These glycosides, and particularly the glucosides, are known as anthocyanins and are present in the fruits of bilberry, vine, elder, currant, bramble and raspberry.

We have now found that a class of flavylium salts which includes both the anthocyanidines which can be prepared by hydrolysing naturally-occurring anthocyanins and synthetic analogues thereof are endowed with remarkable cicatrising and epithelium-regenerating properties which render them particularly useful in the treatment of cutaneous wounds, topid sores, and external and internal ulcers. Also the flavylium salts have been found to possess distinct anti-inflammatory, vasoprotective, hypolipaemic, hypocholesterolaemic and hypoglycaemic activities.

According to the present invention there are provided pharmaceutical compositions comprising a pharmaceutically acceptable diluent or carrier and as active ingredient a flavylium salt having the formula

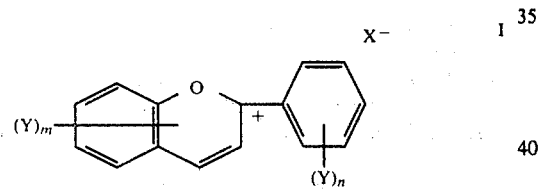

wherein each Y, which may be the same or different represents —OH or —OR wherein R is an alkyl group containing 1 to 6 carbon atoms, m is 0 or an integer from 1 to 6 and n is 0 or an integer from 1 to 5, the sum of m and n being from 1 to 11 and X is a pharmaceutically acceptable cation, The flavylium salts used in the compositions according to the invention frequently have extremely low toxicities which renders them particularly useful for prolonged treatments.

Clinically, the flavylium salts may be administered singly or in the form of mixtures with one another, in the pure state or in the form of crude or partially purified extracts, for example extracts of the crude product obtained by hydrolysis of naturally-occurring mixtures of anthocyanins. Preferably at least a portion of extracted materials other than the anthocyanidines are eliminated from the extracts.

Conveniently, since they may be obtained readily by hydrolysis of glycosides contained in common fruit the flavylium salts used in the pharmaceutical compositions of the invention are anthocyanidines selected from cyanidine, peonidine, delphinidine, petunidine, malvidine and pelargonidine which may be represented by the following formula:

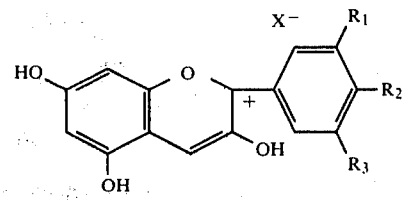

wherein:
$R^1 = R^2 = -OH$ and $R^3 = H$ (cyanidine)
$R^1 = -OMe$, $R^2 = -OH$ and $R^3 = H$ (peonidine)
$R^1 = R^2 = R^3 = OH$ (delphinidine)
$R^1 = OMe$ and $R^2 = R^2 = R^3 = OH$ (petunidine)
$R^1 = R^3 = -OMe$ and $R^2 = -OH$ (malvidine)
$R^2 = -OH$ and $R^1 = R^3 = H$ (pelargonidine)

Particular classes of pharmaceutical compositions according to the invention are those containing salts having the following formulae:

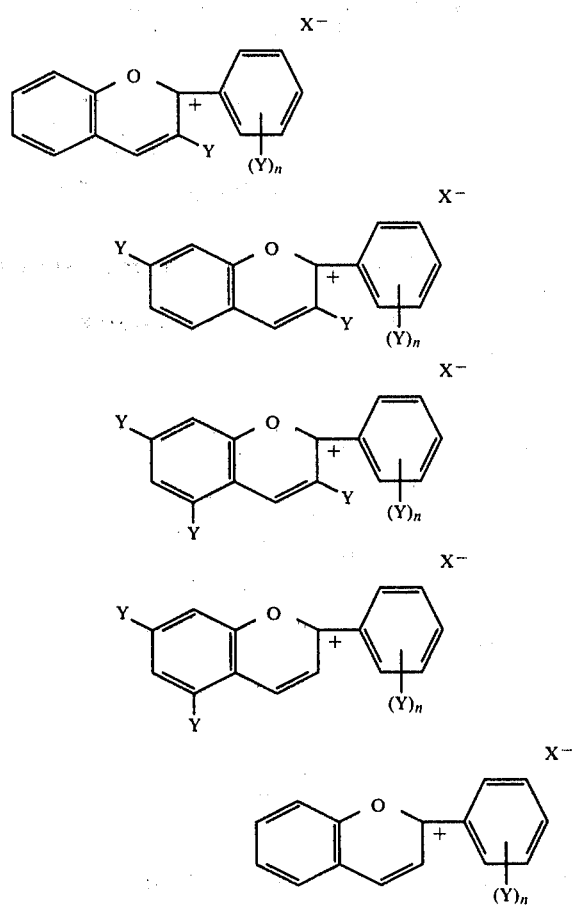

In the above formulae the group

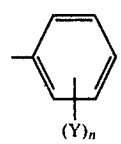

preferably has one of the following structure

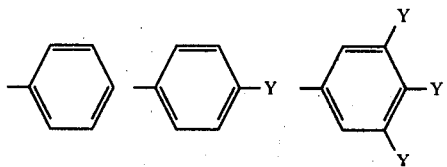

Thus a further preferred class of compounds according to the invention are those having the following formulae:

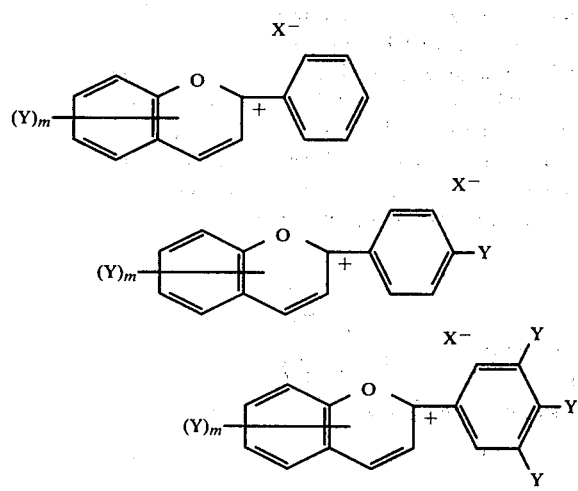

The groups Y in the above formulae are preferably selected from H, OH and OMe.

Thus if the flavylium compounds are represented by the formula

A⁺....B wherein A⁺ represents the group

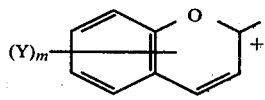

and B represents

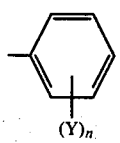

the group A⁺ is preferably selected from

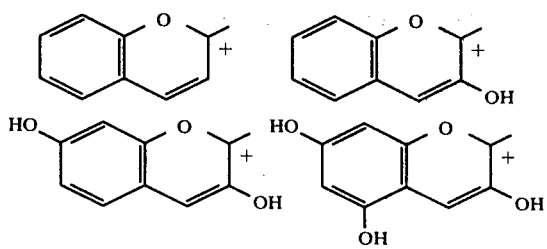

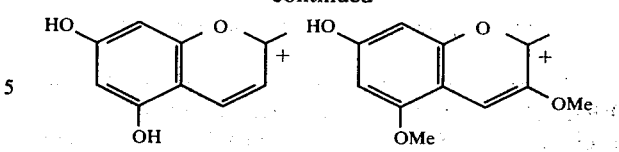

and the group B is preferably selected from

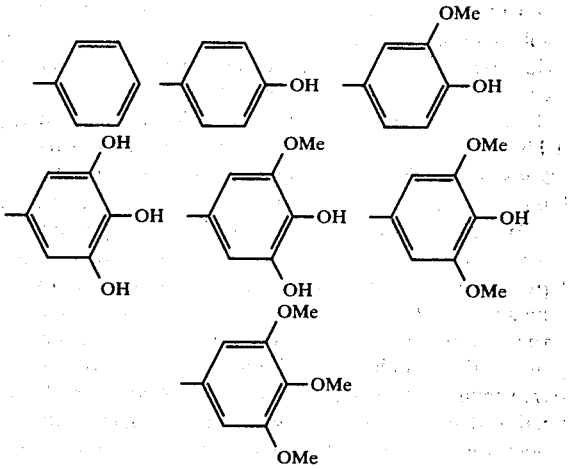

The flavylium compounds may be associated with any pharmaceutically acceptable anion X⁻, e.g. chloride, sulphate, phosphate, acetate, hydroxyl etc.

A particularly preferred class of compounds are those in which at least one of the 3, 5 and 7 positions is unsubstituted.

Flavylium salts suitable for incorporation into pharmaceutical compositions according to the invention may be prepared by known procedures, for example by the condensation reactions reported by A. Robertson and R. Robertson, J. Chem. Soc. 1526, 1928; A. Robertson, R. Robinson and J. Sugiura, J. Chem. Soc. 1533, 1928; S. Murakami and R. Robinson, J. Chem. Soc. 1537, 1928; W. Bradley and R. Robertson J. Chem. Soc. 1541, 1928.

More specifically, flavylium salts of formula I substituted in the 3-position may be prepared by condensing salicylaldehyde or a derivative thereof of formula

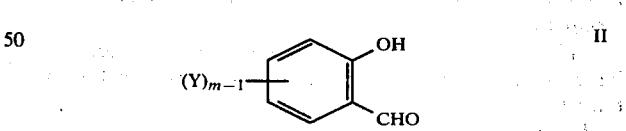

with omega-acyloxy-acetophenone or a derivative thereof of formula

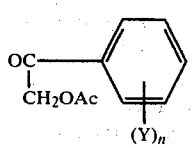

wherein Y, m and n are as defined above and Ac is an acyl radical.

Similarly, flavylium salts of formula I unsubstituted in the 3-position may be prepared by condensing salicylaldehyde or a derivative thereof of formula II defined above with acetophenone or a derivative thereof of formula IV

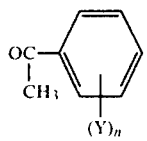

wherein Y and n are as defined above. If desired, any hydroxyl groups representing the groups Y which are likely to interfere with the reactions may be protected and subsequently converted to free hydroxyl groups in a manner known per se.

Thus the production of 3-hydroxyflavylium chloride and 7-hydroxyflavylium chloride are depicted in the following schemes:

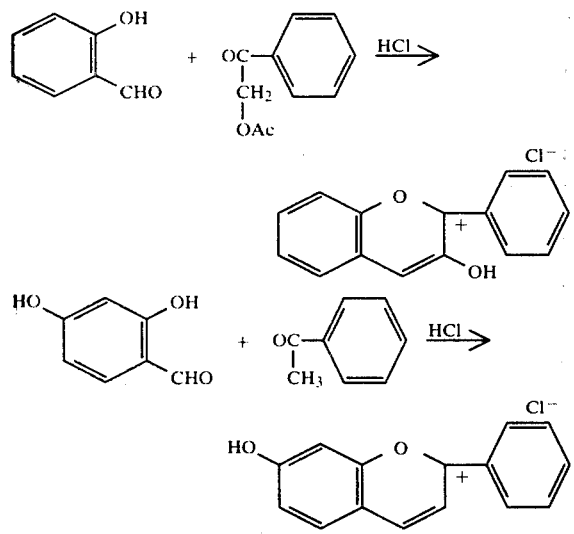

The above condensation reactions are generally carried out in the presence of a strong mineral acid and the immediate products are the salts of these acids. The salts may be converted to salts of other acids by conventional procedures.

Alternatively, where appropriate, pharmaceutical compositions according to the invention may be prepared by extracting an anthocyanin from a plant tissue, hydrolysing the anthocyanin to form an anthocyanidine, purifying the anthocyanidine and admixing the anthocyanidine with a pharmaceutically acceptable excipient.

The particular galenic form of the compositions of the invention depends on the intended route of administration and the condition to be treated and such forms may be amorphous or in the form of shaped dosage units. Examples include sterile liquids suitable for parenteral administration, forms suitable for oral administration (e.g. tablets, capsules, solutions or suspensions); forms suitable for insertion into a body cavity (e.g. anal or vaginal suppositories); forms suitable for topical administration (e.g. ointments, creams, gels and aqueous solutions or suspensions) and dentifrices.

In formulating compositions according to the invention, a wide range of excipients may be used, the nature of which will depend, of course, on the intended mode of application of the composition. Examples include preservatives and buffering, thickening, suspending, stabilising, wetting, emulsifying, colouring and flavouring agents and in particular carboxy vinyl polymers, propylene glycol, ethyl alcohol, water, cetyl alcohol, saturated vegetable triglycerides, fatty acid esters or propylene glycol, triethanolamine, glycerol, starch, sorbitol, bentonite, carboxymethyl cellulose, laurylsulphate, dicalcium phosphate, powdered silicia, lecithin etc.

Frequently, more than one diluent or carrier is advantageously used.

The compositions of the invention have been found to be particularly useful in the treatment of wounds, gastric and duodenal ulcers, inflammatory conditions of the mouth and throat, pathogenic conditions of the vascular system and disorders caused by impaired lipidic and glycidic metabolism.

This invention also includes a process for producing the compounds defined above which comprises bringing a compound of formula (I) into a form suitable for pharmaceutical administration, for example by admixing the active ingredient with one or more excipients and/or conversion to one of the galenic forms referred to above.

The invention also provides a method of eliciting a cicatrising, epithelium-regenerating, anti-inflammatory, vasoprotective, hypolipaemic, hypocholesterolaemic or hypoglycaemic response in a subject, which comprises administering to the subject an effective dose of a flavylium salt of formula I, preferably from 1 to 100 mg/kg and most preferably 5 to 50 mg/kg per day.

The compositions according to the invention preferably contain at least 0.2% and most preferably at least 0.5% by weight of flavylium salt of formula I. More concentrated compositions are preferred for internal (i.e. enteral or parenteral) administration, particularly those containing at least 1% and more particularly at least 5% by weight of flavylium salt. The compositions may be administered at a daily dosage rate of from 1 to 100 mg/kg, preferably 5 to 50 mg/kg of flavylium salts.

The following Preparations illustrate the production of substituted flavylium compounds of formula I which may be used as active ingredients in the production of pharmaceutical compositions according to the invention.

PREPARATION 1

4'-Hydroxyflavylium chloride 122 g of Salicylaldehyde and 136 g of 4-hydroxyacetophenone were dissolved in a four-necked one-liter flask equipped with a mechanical stirrer and containing 400 ml of anhydrous ethyl acetate. Under agitation and at room temperature, a stream of dry hydrochloric acid was passed into the solution in such manner that saturation was completed in the course of one hour. The mixture was left under agitation for 24 hours, during which precipitation of the reaction product began. Filtration was carried out, the product dried at 40° C. in the presence of KOH and recrystallisation carried out twice from methanol. There were obtained 179 g of 4'-hydroxyflavylium chloride.

Molecular ion of the corresponding quinoline silyl derivative: M/e 293: Found: C, 68.99; H, 4.54; Cl, 12.92; $C_{15}H_{11}ClO_2$ requires: C, 69.64; H, 4.29; Cl, 13.70.

PREPARATION 2

3,7-Dihydroxyflavylium chloride 79 g of 2,4-dihydroxybenzaldehyde were dissolved at room temperature in 800 ml of anhydrous ethyl acetate and 106 g of omega-acetoxyacetophenone were added to the solution. The reaction mixture was brought to 0° C. under agitation and gaseous hydrochloric acid added to saturation. After standing for 24 hours at room temperature, crystallisation of the product began and it was filtered and dried at 40° C. in the presence of NaOH. There were obtained 95 g of 3,7-dihydroxyflavilium chloride.

Molecular ion of the corresponding quinoline silyl derivative: m/e 381: Found: C, 64.72; H, 4.19; Cl, 11.83; $C_{15}H_{11}ClO_3$ requires: C, 65.59; H, 4.04; Cl, 12.91.

PREPARATION 3

3-Hydroxyflavylium chloride 88 g of salicylaldehyde were dissolved in 300 ml of anhydrous ethyl acetate together with 132 g of omega-acetoxyacethophenone. The solution was cooled to 0° C. and saturation with gaseous HCl commenced, which took about one hour. The mixture was then left at 4° C. for 48 hours and the crystallised solid filtered off, this consisting of 106 g of 3-hydroxyflavylium chloride.

Molecular ion of the corresponding quinoline silyl derivative: m/e 293: Found: C, 68.72; H, 4.17; Cl, 12.86; $C_{15}H_{11}ClO_2$ requires: C, 69.64; H, 4.29; Cl, 13.70.

PREPARATION 4

3,4'-dihydroxyflavylium chloride 23.2 g of salicylaldehyde and 45 g of omega-acetoxy(4-acetoxy)-acetophenone were dissolved in 300 ml of anhydrous ethyl acetate. The solution was cooled to −5° C., saturated with gaseous hydrochloric acid and left at 4° C. for 48 hours. 35.1 g of crystallised product constituted by 3,4'-dihydroxyflavylium chloride was filtered off.

Molecular ion of the corresponding quinoline silyl derivative: m/e 381: Found: C, 63.82; H, 3.97; Cl, 11.84; $C_{15}H_{11}ClO_3$ requires: C, 65.59; H, 4.04; Cl, 12.91.

PREPARATION 5

3,5,7-Trihydroxy-3',4',5'-trimethoxyflavylium chloride

A solution containing 70 g of (2-O-benzoyl-)2,4,6-trihydroxybenzaldehyde and 95 g of (omega-acetoxy)-3,4,5-trimethoxyacetophenone in 1600 ml of anhydrous ethyl acetate was saturated at room temperature with gaseous HCl. On standing at room temperature, 104 g of product were filtered off after 24 hours and this was redissolved in 5.5 l of methanol and 680 ml of concentrated aqueous hydrochloric acid added. The mixture was left under reflux for 12 hours. It was then cooled and concentrated under vacuum until crystallisation began. After standing at 4° C. for 24 hours, filtration was carried out, the product washed with 200 ml of acetone and dried. There were obtained 76 g of the title compound.

Molecular ion of the corresponding quinoline silyl derivative: m/e 559: Found: C, 55.83; H, 4.32; Cl, 8.96; $C_{18}H_{17}ClO_7$ requires: C, 56.78; H, 4.50; Cl, 9.31.

PREPARATION 6

3,7,4'-Trihydroxyflavylium chloride 96.6 of 4-hydroxy-omega-acetoxyacetophenone and 65.7 g of 2,4-dihydroxybenzaldehyde dissolved in 1 liter of anhydrous ethyl acetate were saturated at room temperature with gaseous HCl. The solution was left under agitation for three hours at room temperature and then at 4° C. for twelve hours. The crystallised solid was then filtered off. There were obtained 142 g of 3,7,4'-trihydroxylflavylium chloride.

Molecular ion of the corresponding quinoline silyl derivative: m/e 469: Found: C, 59.73; H, 3.96; Cl, 11.74; $C_{15}H_{11}O_4Cl$ requires: C, 61.98; H, 3.81; Cl, 12.20.

PREPARATION 7

3,5,7-trihydroxyflavylium chloride 240 g of (2-O-benzoyl)-2,4,6-yrihydroxybenzaldehyde and 178 g of omega-acetoxyacetophenone were dissolved in 3 liters of anhydrous ethyl acetate. Under agitation, HCl was bubbled in to saturation. The solution was left to stand for 24 hours and yielded 175 g of crystallised product, which was redissolved in 7 liters of methyl alcohol containing 430 ml of concentrated hydrochloric acid. The solution obtained was refluxed for 20 hours, then concentrated until crystallisation begins and left for 24 hours at 4° C. The 3,5,7-trihydroxyflavylium chloride obtained weighed 98 g.

Molecular ion of the corresponding quinoline silyl derivative: m/e 469: Found: C, 62.31; H, 3.69; Cl, 11.91; $C_{15}H_{11}O_4Cl$ requires: C, 61.98; H, 3.81; Cl, 12.20.

The following Examples illustrate the production flavylium salts by hydrolysis of anthocyanins (Examples 1 and 2) and Example 3 illustrates the production of pelargonidine by a synthetic method.

EXAMPLE 1

Preparation of anthocyanidines from elder anthocyanins (A) Extraction from elder 13.5 kg of fresh ripe elder fruits were extracted at room temperature with anhydrous methanol containing 1% of hydrochloric acid. The extracts were concentrated in vacuo to small volume and an aqueous solution of 30% of neutral lead acetate added with agitation. An abundant precipitate was obtained which was filtered and washed with water. 200 g. of crude lead salts were obtained which were then suspended with agitation in 600 ml of anhydrous methanol containing hydrochloric acid, agitated at room temperature and the insoluble material eliminated by filtration.

The methanolic solution was then concentrated in vacuo at low temperature to small volume and subsequently poured with agitation into ether. The precipitate was filtered and dried in vacuo at room temperature. 30 g. of glucosides were obtained, equivalent to 15% cyanidine.

(B) Formation of crude cyanidine 30 g. of glucosides equivalent to 15% cyanidine were dissolved in a mixture constituted by methanol and concentrated hydrochloric acid in the ratio 8:2. Heating was effected under reflux for 3 hours. The solution was then diluted with water and concentrated in vacuo until complete elimination of the methanol. A precipitate was obtained which was filtered and washed with water.

After drying, 6 g. of crude hydrolysate was obtained containing 20% cyanidine.

(C) Purification of the cyanidine

The crude 20% cyanidine was purified by chromatography on Sephadex LH 20, eluting with 95% ethanol containing 1% of concentrated hydrochloric acid.

Although anthocyanidines for incorporation in pharmaceutical compositions according to the invention are most conveniently prepared by hydrolysis of fruit anthocyanins (anthocyanosides), for example as described above, they may also be obtained synthetically by reduction of quercetin and its derivatives or rutin (L. Bauer, Chem. and Ind. 1954, 433-4; H.G.C. King, J. Chem. Soc. 1957, 3901-3). Other methods reported in literature enable cyanidine to be obtained from epicatechin pentaacetate (A.K. Ganguli et altri Proc. Indian Aca. Sci., 46A, 25-8, 1957) and from catechin and its derivatives (J. Lavollary, Compt. Rend. 217, 86-8, 1943; H. Apple J. Chem. Soc. 1935, 426-9).

Moreover cyanidine can be obtained by acid hydrolysis of oligomers (polymers of low molecular weight, generally dimers) of catechins (T.A. Geissman and H.F.K. Dittmar Phytochemistry, 1965, vol. 4 pp 359-368).

EXAMPLE 2

Preparation of anthocyanidines from bilberry

Using the procedure used in Example 1, an extract was obtained rich in anthocyanosides equivalent to not less than 25% in total anthocyanidines (malvidine, delphinidine, cyanidine, peonidine and petunidine).

Subsequently the extract was hydrolysed and the anthocyanidines are purified by the following procedure:

The anthocyanosides were dissolved in a mixture of methanol and concentrated hydrochloric acid in the ratio of 8:2, and hydrolysed by means of boiling under reflux for 3 hours. The precipitate formed was cooled and filtered. The liquid was then concentrated in vacuo to eliminate all the methanol, and four extractions with isoamyl alcohol were effected on the concentrate. The reunited isoamyl extracts were concentrated in vacuo and precipitated with agitation in ethyl ether. After filtration and drying, anthocyanidines at 50-60 percent were obtained.

EXAMPLE 3

Synthesis of Pelargonidine Chloride 24 g of 2,4,6-trihydroxybenzaldehyde 2-O-benzoate were dissolved by warming in 500 ml of ethyl acetate and 20 g of p-hydroxyacetoxyacetophenone added. Gaseous hydrochloric acid was introduced to saturation and the mixture kept at room temperature overnight. The obtained solid was then dissolved in 3 liters of methanol, 150 ml of conc. aqueous HCl added and the mixture boiled under reflux for 6 hours. The product was then evaporated under vacuum to 250 ml and allowed to crystallise at 4° C. Yield 14 g of pelargonidine chloride.

The following experimental data illustrates the pharmacological properties of representative examples of flavylium salts which may be incorporated into pharmaceutical compositions according to the invention.

(1) Hyperlipaemia induced by olive oil

Hyperlipaemia was induced in rats which had been fasted for 16 hours by administering olive oil 3 hours prior to sacrifice, at a dose of 2 ml/hg orally.

The substances under test were administered either intraperitoneally (i.p.) or orally (os) one hour prior to sacrificing the rats in the experiments reported in Tables 1 to 4 and 2 hours prior to sacrificing the rats in the experiments reported in Table 5. The concentrations of non-esterified fatty acids (NEFA) and triglycerides in the blood plasma were determined for the experimental subjects and for control rats to which had been administered 0.9% sodium chloride. The results of these tests are given in the following Tables 1 to 5.

TABLE 1

Effect upon hyperlipaemia induced by olive oil in male Morini rats of mean weight 180g

| | TREATMENT | Dose mg/kg (i.p.) | Number of animals | NEFA $\mu$Eq/l | Triglycerides mg/100 ml |
|---|---|---|---|---|---|
| A | Controls 0.9% NaCl 0.5 ml/hg | — | 6 | 648.24 ± 66.06 | 186.90 ± 9.51 |
| B | 3,4'-dihydroxyflavylium chloride | 25 | 6 | 480.15 ± 47.16 (−26.0) | 52.63 ± 4.58* (−71.8) |
| C | 3-hydroxyflavylium chloride | 25 | 6 | 549.89 ± 47.70 (−15.2) | 109.16 ± 25.66** (−41.6) |
| D | 3,7-dihydroxyflavylium chloride | 25 | 6 | 523.07 ± 26.86 (−20.0) | 61.88 ± 9.23* (−66.9) |

*Significantly different (p < 0.01) from the mean obtained from group A according to Student's "t" test
**Significantly different (p < 0.05) from the mean obtained from group A according to Student's "t" test
Note:
In parentheses, the percentage difference from the controls.

TABLE 2

Effect upon hyperlipaemia induced by olive oil in male Morini rats of mean weight 170g

| TREATMENT | Dose mg/kg (os) | NEFA $\mu$Eq/l | Triglycerides mg/100ml |
|---|---|---|---|
| A Controls 0.9% NaCl 1ml/hg | — | 914.7 ± 32.0 | 353.6 ± 29.2 |
| B 5,7-dihydroxy-flavylium chloride | 100 | 696.2 ± 24.2* (−23.9) | 237.5 ± 20.3* (−32.8) |

*Significantly different (p < 0.01) from the mean obtained from group A according to Student's "t" test.
Note:
In parentheses, the percentage difference from the controls.

TABLE 3

Effect upon hyperlipaemia induced by olive oil in male Morini rats of mean weight 170g.

| TREATMENT | Dose mg/kg (i.p.) | NEFA $\mu$Eq/l | Triglycerides mg/100ml |
|---|---|---|---|
| A Controls 0.9% NaCl | — | 1106.3 ± 32.9 | 255.6 ± 15.2 |

TABLE 3-continued

Effect upon hyperlipaemia induced by olive oil in male Morini rats of mean weight 170g.

| TREATMENT | Dose mg/kg (i.p.) | NEFA μEq/l | Triglycerides mg/100ml |
|---|---|---|---|
| B 0.5ml/hg 5,7-dihydroxy-flavylium chloride | 25 | 625.5 ± 12.5* (−43.5) | 68.2 ± 9.2* (−43.5) |

*Significantly different (p < 0.01) from the mean obtained from group A according to Student's "t" test
Note:
In parentheses, the percentage difference from the controls.

TABLE 4

Effect upon hyperlipaemia induced by olive oil in male Wistar and Morini rats of mean weight 175g

| TREATMENT | Dose mg/kg (i.p.) | Number of Animals | NEFA μEq/l | Triglycerides mg/100ml |
|---|---|---|---|---|
| A Controls 0.9% NaCl 0.5mg/hg | — | 9 | 1064.4 ± 39.6 | 368.35 ± 41.6 |
| B Trihydroxy trimethoxy flavylium chloride 644RF | 25 | 25 | 683.2 ± 13.5* (−35.8) | 75.2 ± 20.3* (−79.6) |

*Significantly different (p < 0.01) from the mean obtained from group A according to Student's "t" test.
Note:
In parentheses, the percentage difference from the controls.

TABLE 5

Effect upon hyperlipaemia induced by olive oil in male Wistar and Morini rats of mean weight 175g

| TREATMENT | Dose mg/kg(as) | Number of Animals | NEFA μEq/l | Triglycerides mg/100ml |
|---|---|---|---|---|
| A Controls 0.9% NaCl 1ml/hg | — | 8 | 1056.5 ± 29.3 | 312.8 ± 33.6 |
| B 5,7-dihydroxy flavylium chloride 628RF | 100 | 8 | 775.4 ± 20.7* (−26.6) | 123.9 ± 11.1* (−60.4) |
| C Trihydroxy trimethoxy flavylium chloride 644RF | 100 | 9 | 903.8 ± 30.0*ᵒ (−14.5) | 173.9 ± 17.7*ᵒ (−44.4) |

*Significantly different (p < 0.05) from the mean obtained from group A according to Student's "t" test.
ᵒSignificantly different (p < 0.05) from the mean obtained from group B according to Student's "t" test.
Note:
In parentheses, the percentage difference from the controls.

(2) Hyperlipaemia induced by Triton WR 1339

Hyperlipaemia was induced by intravenous administration of 225 mg/kg of Triton WR 1339 in male Sprague-Dawley and C. River rats of mean weight 200 g 8 hours prior to sacrifice.

The substances under test were injected intraperitoneally twice: the first administration immediately after the Triton and the second 4 hours later.

The results of the tests are given in the following Table 6.

TABLE 6

Effect upon hyperlipaemia induced by Triton WR 1339

| TREATMENT | Dose mg/kg twice daily | Number of Animals | NEFA μEq/l | Triglycerides mg/100ml |
|---|---|---|---|---|
| A Controls 0.9% NaCl 0.5ml/hg | — | 12 | 650.5 ± 29.6 | 170.0 ± 4.9 |
| B 5,7-di-hydroxy flavylium chloride 628 RF | 50 | 12 | 480.3 ± 33.4* (−26.2) | 163.8 ± 5.5 (−3.6) |
| C Trihydroxy trimethoxy flavylium chloride 644 RF | 50 | 12 | 437.7 ± 33.8* (−32.7) | 141.7 ± 3.7*ᵇ (−16.6) |

*Significantly different (p < 0.05) from the mean obtained from group A according to Student's "t" test.
ᵇSignificantly different (p < 0.05) from the mean obtained from group B according to Student's "t" test.
Note:
In parentheses, the percentage difference from the controls.

The following experimental data illustrates the pharmacological properties of anthocyanidines:

I. Anti-ulcer activity - Shay's ulcer in the rat

In Shay's ulcer in the rat, the oral administration of bilberry anthocyanidines at doses of 25 and 50 mg/kg five times, at 48, 33, 22 and 9 hours prior to the ligature of the pylorus and 1 hour after the operation, was found to diminish the ulcer index observed with the controls, by 28 and 39 percent respectively. (See Table 7).

TABLE 7

Anti-ulcer activity - Shay's gastric ulcer in the rat

| TREATMENT | Dose mg/kg (1) | Number of animals | Number of ulcers of each class (2) | | | | | Ulcer Index | Variation of Ulcer Index (3) | Number non-ulcerated stomachs |
|---|---|---|---|---|---|---|---|---|---|---|
| | | | I | II | III | IV | V | | | |
| Controls (water) | — | 19 | 295(295) | 44(220) | 15(150) | 2(40) | 17(340) | 55 | — | — |
| Bilberry anthocyanidines | 25 | 18 | 100(100) | 20(100) | 13(130) | 9(180) | 10(200) | 39.5 | −28 | 11 |
| | 50 | 18 | 271(271) | 21(105) | 7(70) | 3(60) | 5(100) | 33.6 | −39 | 5 |

(1) Doses administered orally 5 times, 48, 33, 22 and 9 hours prior to ligature of the pylorus and 1 hour after
(2) In parentheses, the product of the number of the ulcers and the value of the individual classes according to the evaluation criterion of Keyrilainen T.O. and Paasonen M.K. (Acta Pharmacel. et Texicol. 13, 22, 1957)
(3) Percentage reduction compared with controls

II. Activity upon lipidic metabolism

(1) Hyperlipaemia induced by olive oil

Hyperlipaemia was induced by orally administering olive oil to male Sprague-Dawley rats of mean weight of 165 g. which had been fasted for 16 hours. The administration of olive oil was effected 3 hours prior to sacrifice, at a dose of 2 ml/kg orally.

Bilberry anthocyanidines and cyanidine obtained from elder fruit were administered intraperitoneally 1 hour prior to the administration of the olive oil in equal strength doses dissolved in 0.5 ml/kg of physiological solution. Table 8 shows that the bilberry anthocyanidines significantly diminish the free fatty acids and the triglycerides respectively by 36.60 and 86% in comparison with the controls, and that the cyanidine obtained from elder diminishes the free fatty acids and the triglycerides respectively by 32.70 and 67.90%, again in comparison with the controls.

TABLE 8

Effect upon hyperlipaemia induced by olive oil

| TREATMENT | Dose mg/kg | Number of animals | NEFA* $\mu$Eq/l | Triglycerides mg/100ml |
|---|---|---|---|---|
| A Controls | — | 16 | 1013.22 ± 44.30 | 384.52 ± 42.34 |
| B 58% anthocyanidines from bilberry | 43.1 | 16 | 642.33 ± 27.44$^o$ (−36.60) | 53.73 ± 6.24$^o$ (−86.00) |
| C 32% cyanidine from elder | 72.12 | 16 | 681.73 ± 25.21$^o$ (−32.70) | 123.62 ± 36.68$^o$ (−67.90) |

*Non-esterified fatty acids
$^o$Significantly different ($p < 0.001$) from the mean obtained from group A according to Student's "t" test
Note:
In parentheses, the percentage difference from the controls.

TABLE 9

Effect upon hyperlipaemia induced by Triton WR 1339

| TREATMENT | Dose mg/kg | Number of animals | Triglycerides mg/100ml | Total cholesterol mg/100 |
|---|---|---|---|---|
| A Controls | — | 8 | 621.56 ± 36.87 | 189.93 ± 11.76 |
| B 58% Anthocyanidines from bilberry | 21.5 × 2 | 8 | 437.85 ± 26.01$^{oo}$ (−29.56) | 159.50 ± 3.20$^o$ (−16.03) |
| C 32% cyanidine from elder | 36.6 × 2 | 8 | 474.59 ± 35.06$^o$ (−23.65) | 158.28 ± 6.58$^o$ (−16.67) |

$^o$Significantly different ($p < 0.05$) from the mean obtained with the controls according to Student's "t" test
$^{oo}$Significantly different ($p < 0.01$) from the mean obtained with the controls according to Student's "t" test
Note:
In parentheses the percentage difference from the controls

(2) Hyperlipaemia induced by Triton WR 1339

Hyperlipaemia was induced by intravenous administration of 225 mg/kg, 0.5 ml/kg of Triton WR 1339 dissolved in physiological solution, in male Sprague-Dawley rats of mean weight 210 g. which had been fasted for 24 hours, 8 hours prior to sacrifice.

The substances under test were injected intraperitoneally twice: the first administration simultaneously with the Triton and the second 4 hours later, in equal-strength doses dissolved in 0.5 ml/kg of physiological solution.

From Table 3 it can be seen that bilberry anthocyanidines significantly diminish the plasma triglycerides and cholesterol respectively to 29.56 and 16.03% in comparison with the controls and that elder cyanidine diminishes these lipids by 23.65 and 16.67% respectively, again in comparison with the controls.

III. Activity upon capillary permeability

The action upon capillary permeability was studied on Sprague-Dawley rats of mean weight of 220 g. which had been fasted 18 hours prior to the experiment according to the method of Ankier and West; Brit. J. Pharmacol. 33, 304, 1968. From Table 4 it can be seen that bilberry anthocyanidines administered experimentally by intraperitoneal route at doses of 9, 18 and 36 mg/kg give a significant diminution of the capillary permeability respectively by 12; 25.2 and 55.4% in comparison with the controls.

Table 11 shows the experimental data obtained by oral treatment with bilberry anthocyanidines. The produce was administered experimentally in two doses and specifically at 36 and 72 mg/kg, and gave a significant inhibition of the capillary permeability of 24.6 and 44.4% in comparison with controls.

TABLE 10

Capillary permeability induced by bradykinin in the rat

| TREATMENT mg/kg | | Evans Blue μg | Inhibition per cent |
|---|---|---|---|
| Controls 0.9% NaCl | 0.5 ml/hg | 16.87 ± 0.20 | — |
| 70% anthocyanidines from bilberry | 9 | 14.85 ± 0.20° | 12 |
| | 18 | 12.63 ± 0.10° | 25.2 |
| | 36 | 7.54 ± 0.30° | 55.4 |

Note:
Bradykinin 2 μg/0.1 ml injected intradermally at 3 points into the depilated abdominal zone of each rat
Treatment with the substances under examination 30 minutes prior to the bradykinin
Sacrifice 30 minutes after the bradykinin
°Significantly different ($p < 0.01$) from the mean obtained with the controls according to Student's "t" test

TABLE 11

Capillary permeability induced by bradykinin in the rat

| TREATMENT mg/kg | μg | Evans Blue per cent | Inhibition |
|---|---|---|---|
| Controls (H₂O) | 1 ml/hg | 15.50 ± 0.54 | — |
| 70% anthocyanidines from bilberry | 36 | 11.70 ± 0.51° | 24.6 |
| | 72 | 8.60 ± 0.58° | 44.4 |

Note:
Bradykinin 2 μg/0.1 ml injected intradermally at 3 points of the depilated abdominal zone of each rat
Treatment with the substances under examination 60 minutes prior to the bradykinin
sacrifice 30 minutes after the bradykinin
°Significantly different ($p < 0.01$) from the mean obtained with the controls according to Student's "t" test Activity upon capillary resistance The capillary resistance was studied in rats subjected to deficiency diet according to the method of Charlier R. et al; Arch. intern. Physiol. Biochem., 71, 1, 1963.

Table 12 shows that the bilberry anthocyanidines used experimentally in two doses by oral route increased the capillary resistance with time and in significant manner.

TABLE 12

Activity upon the capillary resistance of rats subjected to dietary deficiency

| TREATMENT mg/kg/os | | Time from treatment hours | | | |
|---|---|---|---|---|---|
| | | 0 | 2 | 4 | 6 |
| 70% anthocyanidines from bilberry | 36 | 15.5 ± 0.32 | 17.0 ± 0.32° | 17.2 ± 0.14° | 17.2 ± 0.14° |
| | 72 | 15.5 ± 0.32 | 17.3 ± 0.41° | 17.6 ± 0.41° | 17.6 ± 0.41° |

°Significantly different from the time 0 ($p < 0.05$) according to Student's "t" test for non-independent samples

TABLE 13

Effect upon hyperlipaemia induced by olive oil

| | TREATMENT | Dose | Number of Animals | NEFA* μEq/l | Triglycerides |
|---|---|---|---|---|---|
| A | Controls (NaCl 0.9%) | 1ml/hg | 8 | 1056.5 ± 29.3 | 312.8 ± 33.6 |
| B | Pelargonidine chloride | 100mg/kg | 8 | 671.5 ± 27.4 (−36.4)° | 140.4 ± 11.6 (−55.1)° |
| C | Peonidine | 100mg/kg | 8 | 950.5 ± 22.9 (−10.0) | 176.0 ± 21.3 (−43.8)° |

*Non-esterified fatty acids.
°Significantly different ($p < 0.05$) from the mean obtained from group A according to Student's "t" test.
Note:
In parentheses, the percentage difference from the controls.

Pharmaceutical compositions according to the invention may be prepared in accordance with the following formulations:

| Freeze-dried injectable solution | |
|---|---|
| 3,4'-dihydroxyflavylium chloride | 15 mg |
| Excipients (mannite, sodium chloride, sodium ethylene diamino tetraacetate, thiourea) q.s. to | 125 mg |
| Solvent: double-distilled water (pyrogen-free) | 3 ml |

| Capsules | |
|---|---|
| 3-hydroxyflavylium chloride | 50 mg |
| Excipients (mannite, citric acid, sodium chloride, thiourea, sodium ethylene diamino tetraacetate, lactose, methyl cellulose, magnesium stearate) q.s. to | 200 mg |

| Capsules | |
|---|---|
| 3,4'-dihydroxyflavylium chloride | 100 mg |
| Excipients (mannite, citric acid, sodium chloride, thiourea, sodium ethylene diamino tetraacetate, laxtose, methyl cellulose, magnesium stearate) q.s. to | 250 mg |

| Tablets | |
|---|---|
| 3,4'-dihydroxyflavylium chloride | 25 mg |
| Excipients (maize starch, lactose, citric acid, magnesium stearate, thiourea, sugar, talc, gum arabic, magnesium carbonate) q.s. to | 200 mg |

| Freeze-dried injectable solution | |
|---|---|
| 3,7-dihydroxyflavylium chloride | 25 mg |
| Excipients (mannite, sodium chloride, sodium ethylene diamino tetraacetate, thiourea) q.s. to | 125 mg |
| Solvent: double-distilled water (pyrogen-free) | 3 ml |

| Ointment | |
|---|---|
| 3,5,7-trihydroxy-3'4'5'-trimethoxyflavylium chloride | 0.25 g |
| Excipients (cetyl alcohol, saturated vegetable triglycerides, esters of polyethylene glycol 2000 with fatty acids $C_{12}$–$C_{14}$, Tween 80, para-oxy benzoates, sorbitol, carboxy vinyl polymer, sodium sulphite, triethanolamine, lecithin, purified water, lactic acid) q.s. to | 100 g |

| Dentifrice gel | |
|---|---|
| 3,5,7-trihydroxy-3'4',5'-trimethoxyflavylium chloride | 0.125 g |
| Excipients (carboxyvinyl polymer, sorbitol, propylene glycol, sodium sulphite, ethyl alcohol, para-oxy benzoates, sodium lauryl sulphate) q.s. to | 100 g |

| Capsules | |
|---|---|
| Elder anthocyanidines (containing 20% cyanidine) | 125 mg |
| Excipients (mannite, citric acid, sodium chloride, thiourea, sodium ethylene diamino tetraacetate, lactose, methyl cellulose, magnesium stearate) q.s. to | 250 mg |

| Freeze-dried injectable solution | |
|---|---|
| Cyanidine | 15 mg |
| Excipients (mannite, sodium chloride, sodium ethylene diamino tetraacetate, thiourea) q.s. to | 125 mg |
| Solvent: double-distilled water (pyrogen-free) | 3 ml |

| Freeze-dried injectable solution | |
|---|---|
| Bilberry anthocyanidines (50% by weight) | 25 mg |
| Excipients (mannite, sodium chloride, sodium ethylene diamino tetraacetate, thiourea) q.s. to | 125 mg |
| Solvent: double-distilled water (pyrogen-free) | 3 ml |

| Capsules | |
|---|---|
| Grape anthocyanidines (25% by weight) | 100 mg |
| Excipients (mannite, citric acid, sodium chloride, thiourea, sodium ethylene diamino tetraacetate, lactose, | |

| | |
|---|---|
| methyl cellulose, magnesium stearate) q.s. to | 200 mg |
| Tablets | |
| Grape anthocyanidines (60% by weight) | 35 mg |
| Excipients ((maize starch, lactose, citric acid, magnesium stearate, thiourea, sugar, talc, gum arabic, magnesium carbonate) q.s. to | 200 mg |
| Ointment | |
| Bilberry anthocyanidines (50% by weight) | 0.5 g |
| Excipients (cetyl alcohol, saturated vegetable triglycerides, esters of polyethylene glycol 2000 with fatty acids $C_{12}$-$C_{14}$, Tween 80, para-oxy benzoates, sorbitol, carboxy vinyl polymer, sodium sulphite, triethanolamine, lecithin, purified water, lactic acid) q.s. to | 100 g |
| Ointment | |
| Elder anthocyanidines (containing 20% cyanidine) | 1 g |
| Excipients (cetyl alcohol, saturated vegetable triglycerides, esters of polyethylene glycol 2000 with fatty acids $C_{12}$-$C_{14}$, Tween 80, para-oxybenzoates, sorbitol, carboxyvinyl polymer, sodium sulphite, triethanolamine, lecithin, purified water, lactic acid) q.s. to | 100 g |
| Dentifrice gel | |
| Bilberry anthocyanidines (35% by weight) | 0.5 g |
| Excipients (carboxyvinyl polymer, sorbitol, propylene glycol, sodium sulphite, ethyl alcohol, para-oxy benzoates, sodium lauryl sulphate) q.s. to | 100 g |
| Dentifrice paste | |
| Grape anthocyanidines (60% by weight) | 0.5 g |
| Excipients (citric acid, sodium bisulphite, sorbitol, ammonium glycyrrhizinate, maize starch, glycerin, para-oxy benzoates, titanium dioxide, calcium phosphate, sodium lauryl sulphate, flavourings, purified water) q.s. to | 100 g |

We claim:

1. A method of eliciting a cicatrizing response in a subject in need of a cicatrizing response, which comprises administering to the subject an effective dose of a flavylium salt of the structure

$A^+$—B $X^-$ containing at least one hydroxy or methoxy substituent and wherein $A^+$ is selected from the group consisting of

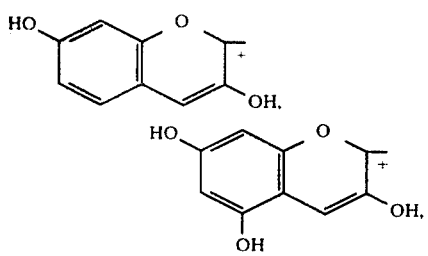

B is selected from the group consisting of

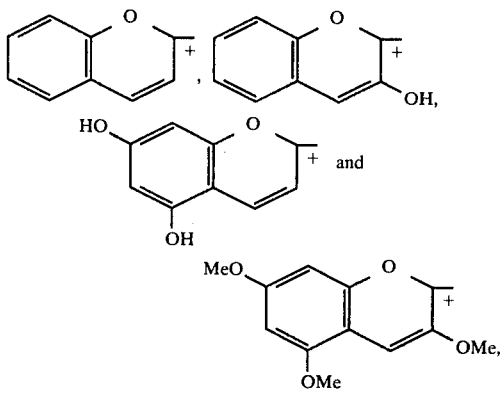

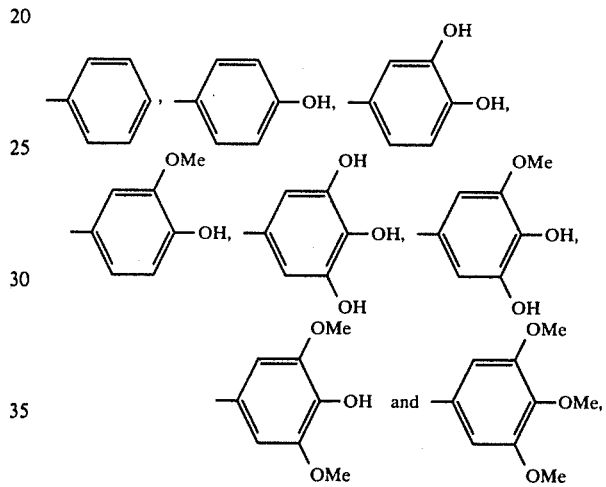

and $X^-$ is a pharmaceutically acceptable anion.

2. A method according to claim 1 in which said effective dose is from 1 to 100 mg/kg per day of said flavylium salt.

3. A method according to claim 2 in which said effective daily dose is from 5 to 50 mg/kg per day of said flavylium salt.

4. A method according to claim 1 in which the flavylium salt is administered in the form of a composition comprising a pharmaceutically acceptable diluent or carrier and as active ingredient a cicatrizing effective quantity of said flavylium salt.

5. A method according to claim 1 in which said flavylium salt is administered as a treatment of wounds, gastric and duodenal ulcers, or inflammatory conditions of the mouth and throat.

* * * * *